US00PP28294P2

(12) United States Plant Patent
Heuger

(10) Patent No.: US PP28,294 P2
(45) Date of Patent: Aug. 15, 2017

(54) ***HELLEBORUS* PLANT NAMED 'COSEH 4000'**

(50) Latin Name: *Helleborus×ericsmithii×Helleborus×hybridus*
Varietal Denomination: COSEH 4000

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 14/999,208

(22) Filed: Apr. 11, 2016

(51) Int. Cl.
*A01H 5/02* (2006.01)

(52) U.S. Cl.
USPC ..... Plt./439

(58) Field of Classification Search
USPC ..... Plt./439
See application file for complete search history.

(56) References Cited

PUBLICATIONS

UPOV hit on *Helleborus* plant named 'COSEH 4000', QZ PBR 20152740, published Feb. 15, 2016.*

* cited by examiner

*Primary Examiner* — Anne Grunberg
(74) *Attorney, Agent, or Firm* — C. A. Whealy

(57) ABSTRACT

A new and distinct cultivar of *Helleborus* plant named 'COSEH 4000', characterized by its upright and mounding plant habit; uniform and freely flowering habit; dark green-colored leaves; freely and early flowering habit; single white-colored flowers with red purple-colored margins; and good garden performance.

2 Drawing Sheets

Botanical designation: *Helleborus×ericsmithii×Helleborus×hybridus.*

Cultivar denomination: 'COSEH 4000'.

BACKGROUND OF THE INVENTION

The present invention relates to a new and distinct cultivar of *Helleborus* plant, botanically known as *Helleborus×ericsmithii×Helleborus×hybridus* and hereinafter referred to by the name 'COSEH 4000'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in November, 2010 of an unnamed selection of *Helleborus×ericsmithii*, not patented, as the female, or seed, parent with an unnamed seedling selection of *Helleborus×hybridus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2012.

Asexual reproduction of the new *Helleborus* plant by divisions in a controlled environment in Glandorf, Germany since February, 2013 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 4000'. These characteristics in combination distinguish 'COSEH 4000' as a new and distinct *Helleborus* plant:

1. Upright and mounding plant habit.
2. Uniform and freely flowering habit.
3. Dark green-colored leaves.
4. Freely and early flowering habit.
5. Single white-colored flowers with red purple-colored margins.
6. Good garden performance.

Compared to plants of the female parent selection, plants of the new *Helleborus* and the female parent selection differ primarily in flower color as plants of the female parent selection have creamy white to pink-colored flowers. Compared to plants of the male parent selection, plants of the new *Helleborus* are more uniform and are more freely flowering.

Plants of the new *Helleborus* can be compared to plants of *Helleborus niger×Helleborus lividus* 'COSEH 710', disclosed in U.S. Plant Pat. No. 21,063. In side-by-side comparisons, plants of the new *Helleborus* differ primarily from plants of 'COSEH 710' in the following characteristics:

1. Plants of the new *Helleborus* have smaller flowers than plants of 'COSEH 710'.
2. Plants of the new *Helleborus* flower earlier than plants of plants of 'COSEH 710'.
3. Plants of the new *Helleborus* and 'COSEH 710' differ in flower color as plants of 'COSEH 710' have light green-colored flowers with reddish pink overtones.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 4000' grown in a container.

The photograph on the second sheet is a close-up view of a typical flower of 'COSEH 4000'.

DETAILED BOTANICAL DESCRIPTION

The aforementioned photographs and following observations, measurements and values describe plants grown during the autumn in 15-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus×ericsmithii×Helleborus×hybridus* 'COSEH 4000'.

Parentage:

*Female, or seed, parent*.—Unnamed selection of *Helleborus×ericsmithii*, not patented.

*Male, or pollen, parent*.—Unnamed seedling selection of *Helleborus×hybridus*, not patented.

Propagation:

*Type*.—By tissue culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Sparse.

Plant description:

*Plant and growth habit*.—Herbaceous perennial; upright and mounding plant habit with flowers held above and beyond the foliar plane; plant shape, roughly flattened globular; moderately vigorous growth habit; moderate growth rate.

*Plant height, soil level to top of foliar plane*.—About 20 cm.

*Plant height, soil level to top of flowers*.—About 31.8 cm.

*Plant diameter* (*area of spread*).—About 38.4 cm.

Leaf description:

*Arrangement*.—Leaves arranged in a basal rosette; leaves palmately compound with typically five to seven leaflets per leaf.

*Leaf length*.—About 16.6 cm.

*Leaf width*.—About 18.6 cm.

*Leaflet length*.—About 11.2 cm.

*Leaflet width*.—About 5.7 cm.

*Leaf shape*.—Palmate; reniform in outline.

*Leaflet shape*.—Ovate, elliptic and obovate.

*Leaflet apex*.—Apiculate.

*Leaflet base*.—Attenuate.

*Leaflet margin*.—Serrate; undulate.

*Leaflet texture and luster, upper surface*.—Smooth, glabrous; slightly rugose; leathery; glossy.

*Leaflet texture and luster, lower surface*.—Smooth, glabrous; slightly rugose; leathery; slightly glossy.

*Leaflet venation pattern*.—Pinnate.

*Leaflet color*.—Developing leaflets, upper surface: Close to N137A. Developing leaflets, lower surface: Close to 147B. Fully developed leaflets, upper surface: Close to darker than between 139A and N189A; venation, close to 147B. Fully developed leaflets, lower surface: Close to 143B to 143C; venation, close to 152A.

*Petioles*.—Length: About 11.5 cm. Diameter: About 5 mm. Strength: Strong. Texture and luster, upper and lower surfaces: Smooth, glabrous; glossy. Color, upper and lower surfaces: Close to N148A, heavily tinged and speckled with close to N199B.

Flower description:

*Flower shape and habit*.—Single rotate flowers arranged solitary or in panicles; freely and uniform flowering habit with about ten flowers per inflorescence and about 40 flowers developing per plant; flowers facing outwardly to slightly nodding.

*Fragrance*.—None detected.

*Natural flowering season*.—Plants begin flowering about ten months after planting; plants flower from autumn into winter in Germany.

*Flower longevity on the plant*.—About ten days; flowers not persistent.

*Flower buds*.—Length: About 2 cm. Diameter: About 1.3 cm. Shape: Ovate. Texture and luster: Glabrous; matte. Color: Close to between 145D and 150D.

*Inflorescence height*.—About 31.6 cm.

*Inflorescence diameter*.—About 30.8 cm.

*Flower diameter*.—About 8 cm.

*Flower depth* (*height*).—About 2.6 cm.

*Petals*.—Transformed into nectaries.

*Sepals*.—Quantity and arrangement: About five, arranged in a single whorl. Length: About 4 cm. Width: About 4 cm. Shape: Broadly ovate. Apex: Obtuse. Base: Cuneate. Margin: Entire. Texture and luster, upper and lower surfaces: Glabrous; matte. Color: When opening, upper surface: Close to NN155A to NN155B. When opening, lower surface: Close to NN155A tinged with close to 157D and 74B. Fully opened, upper surface: Close to N155C; towards the margins, heavily tinged with close to between 64A and 70A; with development, color becoming closer to 147B and margins, tinged with close to N77A. Fully opened, lower surface: Close to 184B and 184C; towards the margins, heavily tinged with close to between 64A and 70A; with development, color becoming closer to slightly darker than N77A.

*Flower bracts*.—Quantity per flower: Typically two. Length: About 6.1 cm. Width: About 3.4 cm. Shape: Ovate. Apex: Acute. Base: Broadly cuneate. Margin: Entire; distally, occasionally serrated; undulate. Color, upper surface: Slightly darker than close to between NN137A and 147A. Color, lower surface: Close to 146A to 146B.

*Peduncles*.—Length: About 26.8 cm. Diameter: About 9 mm. Aspect: About 25° from vertical. Strength: Strong. Texture and luster: Glabrous; slightly glossy. Color: Close to 144 A, speckled with close to 177B.

*Pedicels*.—Length: About 4 cm. Diameter: About 3 mm. Aspect: About 25° from peduncle axis. Strength: Moderately strong. Texture and luster: Glabrous; glossy. Color: Close to 144B, speckled and tinged with close to 152A and 152B.

*Reproductive organs*.—Stamens: Quantity per flower: About 80. Filament length: About 1.8 cm. Filament color: Close to NN155D. Anther shape: Reniform; basifixed. Anther size: About 1.75 mm by 2 mm. Anther color: Close to 2C. Pollen amount: Scarce. Pollen color: Close to 2D. Pistils: Quantity per flower: About four to seven. Pistil length: About 1 cm. Stigma diameter: About 0.3 mm. Stigma shape: Club-shaped. Stigma color: Close to 155A. Style length: About 9.5 mm. Style color: Close to 63D. Ovary color: Close to 150D. Nectaries (transformed petals): Quantity per flower: About 13. Length: About 1.2 cm. Diameter: About 3.5 mm. Shape: Tubular, flattened. Texture and luster, inner surface: Smooth, glabrous; matte. Texture and luster, outer surface: Smooth, glabrous; glossy. Color, immature, inner and outer surfaces: Close to N144D; towards the apex, close to 154B. Color, mature, inner and outer surfaces: Close to 146D; towards the apex, close to 12A.

*Seeds and fruits*.—Seed and fruit development have not been observed on plants of the new *Helleborus*.

Garden performance: Plants of the new *Helleborus* have been observed to have good garden performance and to tolerate rain, wind and to be suitable for USDA Hardiness Zones 5 through 9.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 4000' as illustrated and described.

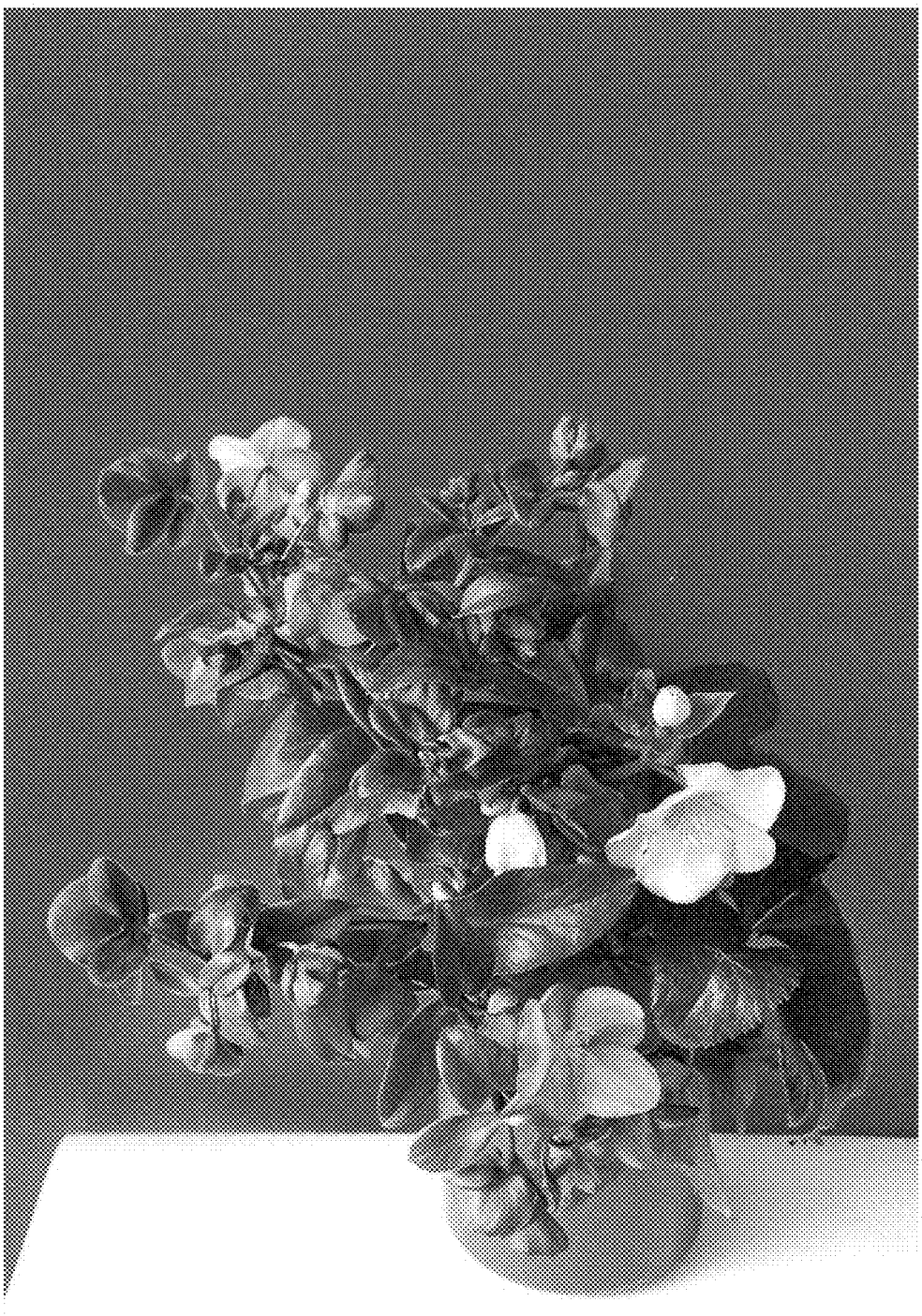

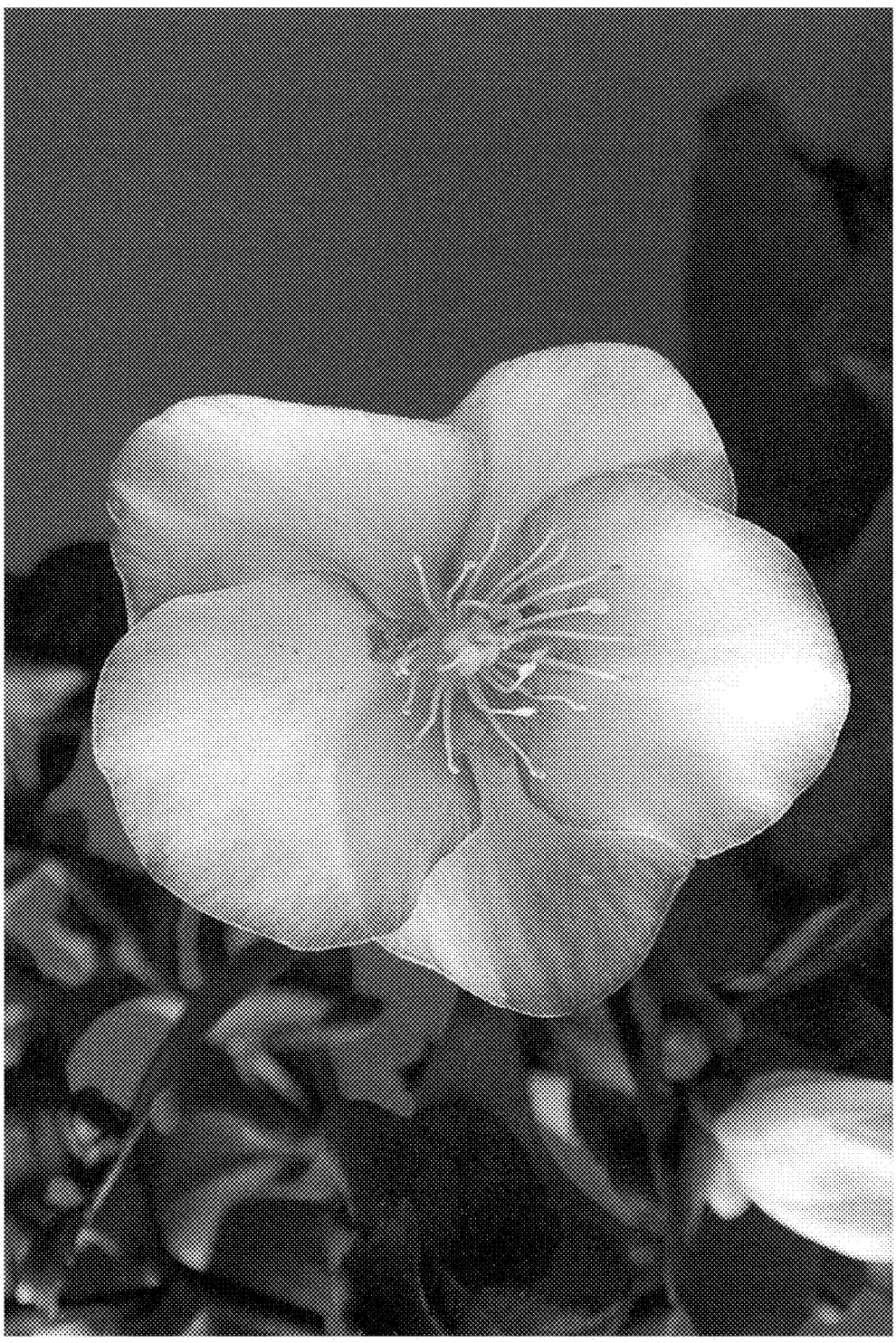

* * * * *